US011681952B2

(12) United States Patent
Fine et al.

(10) Patent No.: US 11,681,952 B2
(45) Date of Patent: *Jun. 20, 2023

(54) SYSTEM FOR AUGMENTING IMAGE DATA OF MEDICALLY INVASIVE DEVICES USING OPTICAL IMAGING

(71) Applicants: Gabriel Fine, Salt Lake City, UT (US); Nathan Silberman, Brooklyn, NY (US)

(72) Inventors: Gabriel Fine, Salt Lake City, UT (US); Nathan Silberman, Brooklyn, NY (US)

(*) Notice: Subject to any disclaimer, the term of this patent is extended or adjusted under 35 U.S.C. 154(b) by 225 days.

This patent is subject to a terminal disclaimer.

(21) Appl. No.: 17/130,938

(22) Filed: Dec. 22, 2020

(65) Prior Publication Data

US 2021/0110566 A1 Apr. 15, 2021

Related U.S. Application Data

(63) Continuation of application No. 16/712,621, filed on Dec. 12, 2019, now Pat. No. 11,062,473, which is a
(Continued)

(51) Int. Cl.
*G06T 7/70* (2017.01)
*G06T 7/00* (2017.01)
(Continued)

(52) U.S. Cl.
CPC ............. *G06T 7/70* (2017.01); *A61B 34/10* (2016.02); *A61B 34/20* (2016.02); *G06K 9/6273* (2013.01);
(Continued)

(58) Field of Classification Search
CPC . G06T 7/70; G06T 7/0016; G06T 2207/1088; G06T 2207/10116;
(Continued)

(56) References Cited

U.S. PATENT DOCUMENTS 5,577,502 A 11/1996 Darrow et al.
5,676,673 A 10/1997 Ferre et al.
(Continued)

FOREIGN PATENT DOCUMENTS

CN 100578511 1/2010

OTHER PUBLICATIONS

American College of Radiology Data Science Institute [online], "FDA Cleared AI Algorithms", retrieved on Dec. 23, 2020, retrieved from URL: https://www.acrdsi.org/DSI-Services/FDA-Cleared-AI-Algorithms, 55 pages.
(Continued)

*Primary Examiner* — Fayyaz Alam
(74) *Attorney, Agent, or Firm* — Barnes & Thornburg LLP

(57) ABSTRACT

A system and method is disclosed for augmenting image data of an invasive medical device using optical imaging. An optical imaging sensor, separate from the invasive medical device, can generate images of the medical device within a patient. A trained model for the invasive medical device can be trained on annotated images of the invasive medical device with orientation and distance information of the invasive medical device. An imaging computer system can apply the trained model to images of the invasive medical device within the patient to determine a current orientation and a current distance of the invasive medical device. The images of the invasive medical device as captured by the optical imaging sensor, visual orientation information representing the current orientation of the invasive medical device, and visual distance information representing the current distance of the invasive medical device within the patient can be displayed.

20 Claims, 9 Drawing Sheets

Related U.S. Application Data continuation of application No. 15/831,132, filed on Dec. 4, 2017, now Pat. No. 10,529,088.

(60) Provisional application No. 62/429,479, filed on Dec. 2, 2016.

(51) Int. Cl.

| | | |
|---|---|---|
| *A61B 34/10* | (2016.01) | |
| *A61B 34/20* | (2016.01) | |
| *G16H 30/20* | (2018.01) | |
| *G06K 9/62* | (2022.01) | |
| *G06T 7/73* | (2017.01) | |
| *G16H 50/50* | (2018.01) | |
| *G06N 3/04* | (2023.01) | |
| *G16H 40/63* | (2018.01) | |
| *G16H 30/40* | (2018.01) | |
| *G06N 3/08* | (2023.01) | |
| *G06V 30/194* | (2022.01) | |
| *G06N 20/00* | (2019.01) | |
| *A61B 90/00* | (2016.01) | |
| *A61F 2/01* | (2006.01) | |

(52) U.S. Cl.
CPC ......... *G06N 3/0445* (2013.01); *G06N 3/0454* (2013.01); *G06N 3/08* (2013.01); *G06T 7/0016* (2013.01); *G06T 7/75* (2017.01); *G06V 30/194* (2022.01); *G16H 30/20* (2018.01); *G16H 30/40* (2018.01); *G16H 40/63* (2018.01); *G16H 50/50* (2018.01); *A61B 2034/102* (2016.02); *A61B 2034/2051* (2016.02); *A61B 2034/2065* (2016.02); *A61B 2090/367* (2016.02); *A61B 2090/376* (2016.02); *A61F 2/01* (2013.01); *A61F 2/0105* (2020.05); *G06N 20/00* (2019.01); *G06T 2207/10072* (2013.01); *G06T 2207/10081* (2013.01); *G06T 2207/10088* (2013.01); *G06T 2207/10116* (2013.01); *G06T 2207/10121* (2013.01); *G06T 2207/10132* (2013.01); *G06T 2207/20084* (2013.01); *G06T 2207/30021* (2013.01)

(58) Field of Classification Search
CPC .......... G06T 2207/10132; A61B 34/10; A61B 34/20; A61B 2034/102; A61B 2034/2051; G16H 30/20; G06K 9/6273; G06K 9/66
See application file for complete search history.

(56) References Cited

U.S. PATENT DOCUMENTS

| | | | |
|---|---|---|---|
| 6,574,493 | B2 | 6/2003 | Rasche et al. |
| 9,171,403 | B2 | 8/2015 | Shapira |
| 9,155,868 | B2 | 10/2015 | Drake et al. |
| 9,179,827 | B2 | 11/2015 | Hastings et al. |
| 9,265,468 | B2 | 2/2016 | Rai et al. |
| 9,675,319 | B1* | 6/2017 | Razzaque ............... A61B 6/037 |
| 9,687,204 | B2* | 6/2017 | Mountney ............ A61B 8/4245 |
| 9,940,545 | B2* | 4/2018 | Rezaee ................ G06K 9/6267 |
| 10,621,737 | B2 | 4/2020 | Piper |
| 10,783,634 | B2 | 9/2020 | Nye et al. |
| 2003/0181809 | A1 | 9/2003 | Hall et al. |
| 2008/0118115 | A1 | 5/2008 | Williamson |
| 2012/0087563 | A1* | 4/2012 | Ionasec ................ G06T 19/006 |
| | | | 382/128 |
| 2013/0072787 | A1* | 3/2013 | Wallace ................ A61B 90/50 |
| | | | 600/424 |
| 2013/0197357 | A1* | 8/2013 | Green ................ A61B 8/0841 |
| | | | 600/424 |
| 2015/0059736 | A1 | 3/2015 | Qiu |
| 2015/0112182 | A1* | 4/2015 | Sharma ................ A61B 5/7264 |
| | | | 600/408 |
| 2015/0182187 | A1* | 7/2015 | Samset ................ A61B 8/4416 |
| | | | 600/424 |
| 2015/0371437 | A1* | 12/2015 | Mansi ..................... G06T 11/60 |
| | | | 382/131 |
| 2016/0063359 | A1 | 3/2016 | Szegedly et al. |
| 2016/0117316 | A1* | 4/2016 | Le ......................... G06N 3/0445 |
| | | | 704/9 |
| 2017/0249536 | A1* | 8/2017 | Hillar ................... G06K 9/6247 |
| 2017/0325896 | A1* | 11/2017 | Donhowe .............. G16H 20/40 |
| 2017/0357753 | A1* | 12/2017 | Mori ...................... G16H 30/20 |
| 2018/0008222 | A1* | 1/2018 | Chen ........................ G06T 7/73 |
| 2018/0060719 | A1* | 3/2018 | Kisilev ................ G06N 3/0454 |
| 2018/0121768 | A1* | 5/2018 | Lin ...................... G06K 9/6215 |
| 2018/0158209 | A1 | 6/2018 | Fine |
| 2018/0235709 | A1* | 8/2018 | Donhowe ................. G06T 7/33 |
| 2018/0240237 | A1* | 8/2018 | Donhowe ............. G06T 7/0014 |
| 2018/0256262 | A1* | 9/2018 | Duindam ............... A61B 34/20 |
| 2018/0260793 | A1* | 9/2018 | Li ........................... G06N 7/005 |
| 2018/0333112 | A1* | 11/2018 | Weber .................. A61B 8/0841 |
| 2019/0142388 | A1 | 5/2019 | Gonyeau |
| 2019/0180136 | A1 | 6/2019 | Bousmalis |
| 2019/0304065 | A1 | 10/2019 | Bousmalis |

OTHER PUBLICATIONS blender.org [online], "About Blender," available on or before Nov. 9, 2015, via Internet Archive: Wayback Machine URL <https://web.archive.org/web/20151109210404/http:/www.blender.org/manual/getting_started/about_blender/introduction.html#key-features>, [retrieved on Nov. 18, 2019], 2 pages.

blender.org [online], "Blender," available on or before Sep. 12, 2016, via Internet Archive: Wayback Machine URL <https://web.archive.org/web/20160912102244/http://www.blender.org/>, [retrieved on Apr. 12, 2019], 11 pages.

blender.org [online], "Modeling," available on or before Nov. 16, 2015, via Internet Archive: Wayback Machine URL <https://web.archive.org/web/20151116191346/http://www.blender.org/manual/modeling/introduction.html>, [retrieved on Nov. 18, 2019], 2 pages.

blender.org [online], "Render," available on or before Nov. 6, 2015, via Internet Archive: Wayback Machine URL <https://web.archive.org/web/20151106190203/http://www.blender.org/manual/render/introduction.html>, [retrieved on Nov. 18, 2019], 2 pages.

McManamon, "Chapter 1: Introduction to LiDAR", LiDAR Technologies and Systems, 2019, 28 pages.

MIMSoftware.com [online], "MIM SurePlan™ LiverY90", retrieved on Sep. 22, 2020, retrieved from URL <https://www.mimsoftware.com/nuclear_medicine/sureplan_liver_y90>, 4 pages.

Moffitt Cancer Center [online], "Internal Radiotherapy", retrieved on Dec. 23, 2020, retrieved from URL: https://moffitt.org/treatments/radiation-therapy/internal-radiotherapy/, 1 page.

Riverain Technologies [online], "ClearRead Xray—Confirm", retrieved on Dec. 23, 2020, retrieved from URL: https://www.riveraintech.com/clearread-xray/xray-confirm/, 5 pages.

Riverain Technologies, "Traditional 510(k) Premarket Notification ClearRead +ConfirmTM", Riverain Technologies, Dec. 2012, 6 pages.

Rohman, "New imaging technique could extend perception of microscopes, endoscopes", Advanced Visualization, Jan. 2019, 3 pages.

SIRTeX.com [online], "About SIR-Spheres microspheres", retrieved on Sep. 22, 2020, retrieved from URL <http://www.sirtex.com/us/clinicians/about-sir-spheres-microspheres/>, 4 pages.

Stella et al., "Image Analysis and Automation of Data Processing in Assessment of Dental X-ray (OPG) Using MATLAB and Excel VBA", Advancement of Machine Intelligence in Interactive Medical Image Analysis, Dec. 2019, pp. 197-214.

Taylor, "AngioDynamics to buy RadiaDyne for radiotherapy devices", MedTech Dive, Sep. 2018, 3 pages.

TechLink [online], "Combined lidar-radar for medical imaging and detection of cancerous tumors", retrieved on Sep. 22, 2020, retrieved from URL <https://techlinkcenter.org/technologies/combined-lidar-

(56) References Cited

OTHER PUBLICATIONS radar-for-medical-imaging-and-detection-of-cancerous-tumors/2411fdbf-f556-41c3-be1c-aeb179f29e54>, 4 pages.

Wu, "Fast Catheter segmentation and tracking based on X-ray fluoroscopic and echocardiographic modalities for catheter-based cardiac minimally invasive interventions", University of London Imperial College of Science, Technology and Medicine Department of Computing, Oct. 2014, 211 pages.

\* cited by examiner

SYSTEM FOR AUGMENTING IMAGE DATA OF MEDICALLY INVASIVE DEVICES USING OPTICAL IMAGING

CLAIM OF PRIORITY

This application is a continuation of U.S. patent application Ser. No. 16/712,621 filed Dec. 12, 2019, which is a continuation of U.S. patent application Ser. No. 15/831,132 filed on Dec. 4, 2017 (now U.S. Pat. No. 10,529,088), which claims priority to U.S. Provisional Application Ser. No. 62/429,479, filed on Dec. 2, 2016, the entire contents of which are hereby incorporated by reference.

BACKGROUND

Various medical procedures involving invasive medical devices require the physical manipulation of these tools for the successful completion of the procedure. These procedures require precision with regard to the correct placement and movement of these devices for (a) completing the procedure at hand in a timely fashion, (b) avoiding harm to the patient, and (c) limiting radiation exposure to the patient and operator. To assist medical practitioners, two-dimensional ("2D") imaging technologies have been developed to provide practitioners with 2D views of their progress in real time. For example, fluoroscopy and ultrasound are imaging technologies that provide practitioners with guidance and orientation in 2D space. Some of these 2D imaging technologies additionally provide practitioners with 2D views of the invasive tools themselves on a graphical display.

SUMMARY

The document generally relates to medical vision tools to provide orientation information for medical devices within 2D image projections, which can be used by practitioners to perform image-guided procedures, including procedures performed by interventionalists (e.g. interventional radiologists, cardiologists, nephrologists, gastroenterologists, etc) and surgeons. Medical practitioners often rely upon technology when performing a medical procedure. A tracking system can be used to provide positioning information for medical instruments with respect to patients, other instruments, and/or reference coordinate systems. Medical practitioners may refer to tracking systems to ascertain the position of the medical instrument, for example, when the instrument is not within the practitioner's line of sight and/or to confirm proper alignment of the instrument. A tracking system may also aid in presurgical planning.

A system and method is disclosed for augmenting image data of an invasive medical device using optical imaging. An optical imaging sensor, separate from the invasive medical device, can generate images of the medical device within a patient. A trained model for the invasive medical device can be trained on annotated images of the invasive medical device with orientation and distance information of the invasive medical device. An imaging computer system can apply the trained model to images of the invasive medical device within the patient to determine a current orientation and a current distance of the invasive medical device. The images of the invasive medical device as captured by the optical imaging sensor, visual orientation information representing the current orientation of the invasive medical device, and visual distance information representing the current distance of the invasive medical device within the patient can be displayed.

In one implementation, a system for augmenting imaging data depicting an invasive medical device includes an invasive medical device configured to be inserted into a patient as part of a medical procedure; an imaging device configured to generate one or more two-dimensional ("2D") images of the invasive medical device within the patient; a database programmed to store a trained model for the invasive medical device, wherein the trained model was generated from one or more machine learning algorithms being trained on annotated 2D images of the invasive medical device with orientation and position information, wherein the trained model is programmed to be used to determine orientation and position information from unannotated 2D images of the invasive medical device; an imaging computer system; and a display to monitor the invasive medical device within the patient, the display being programmed to output (i) the one or more 2D images of the invasive medical device, as generated by the imaging device, and (ii) the current orientation and the current position of the invasive medical device, as determined from application of the trained model to the one or more 2D images. The imaging computer system is programmed to: receive the one or more 2D images of the invasive medical device from the imaging device, access the trained model for the invasive medical device from the database, determine a current orientation and a current position of the invasive medical device within the patient by applying the trained model to the one or more 2D images of the invasive medical device, and output the current orientation and the current position of the invasive medical device.

Such an implementation can optionally include one or more of the following features, which can be combined in any possible permutation of features. The system can further include a training computer system to generate the trained model for the invasive medical device. The training computer system can be programmed to obtain the annotated 2D images of the invasive medical device with orientation and position information, the annotated 2D images depicting the invasive medical device within a patient, the orientation and position information identifying orientations and positions of the invasive medical device in the annotated 2D images, iteratively train a model for the invasive medical device by correlating each of the annotated 2D images to corresponding orientation and position information across one or more model layers using the one or more machine learning algorithms, wherein the iterative training generates the trained model for the invasive medical device, and store the trained model for use by the imaging computer system. At least a portion of the annotated 2D images can be actual images from use of the invasive medical device that have been manually annotated by a practitioner with position and orientation information. At least a portion of the annotated 2D images can be computer generated images simulating use of the invasive medical device within patients as imaged by the imaging device. The one or more machine learning algorithms can include a supervised deep learning algorithm. The trained model can include a long short-term memory model.

The trained model can be specific to the combination of the invasive medical device and the imaging device. Other trained models can be used for other combinations of (i) the invasive medical device or other invasive medical devices and (ii) the imaging device or other imaging devices. The database can store one or more of the other trained models. The imaging device can include an x-ray imaging device and the one or more 2D images comprises one or more x-ray images. The imaging device can include an ultrasound device and the one or more 2D images comprises one or more ultrasound images. The imaging device can include a computerized tomography ("CT") imaging device and the one or more 2D images comprises one or more CT scans. The imaging device can include a magnetic resonance imaging ("MRI") device and the one or more 2D images comprises one or more MRI images. The imaging device can include a nuclear imaging device and the one or more 2D images can include one or more nuclear images. The imaging device can include a magnetic resonance imaging ("MRI") device and the one or more 2D images comprises one or more MRI images. The current orientation can include a current roll, pitch, and yaw of the invasive medical device. The current roll, pitch, and yaw can be in radian space, and the trained model is determined using a cosine distance loss function. The current roll, pitch, and yaw can be discretized and the trained model is determined using a sigmoid-cross entropy. The current position can include (i) anterior and posterior position information, (ii) cranial and caudal position information, and (iii) left and right position information. The current orientation and position of the invasive medical device can be determined from a single image from the one or more 2D images. The current orientation and position of the invasive medical device can be determined from a sequence of images from the one or more 2D images. The current orientation and position of the invasive medical device can be determined from a single image from the one or more 2D images and a reference image for the invasive medical device.

The disclosed techniques, systems, and devices can be used with any of the described imaging modalities with and/or without the administration of contrast (e.g. angiography).

Certain implementations may provide one or more advantages. For example, imaging of medical instruments can be improved, which can allow medical practitioners to more accurately visualize the position and orientation of medical instruments before and/or during medical procedures. This additional and improved information can allow practitioners to more quickly and safely perform medical procedures. For instance, having three-dimensional ("3D") knowledge of both position and orientation of a medical device can allow a practitioner to more successfully, safely, and timely complete many operations. In contrast, 2D imaging technology can inadequately represent the device's position and orientation, which can increase the time it takes practitioners to perform the procedures. Since the amount of radiation that a patient is exposed to is proportional to the duration of the procedure, longer procedures (such as those performed using 2D imaging technology) can increase the amount radiation, which can introduce risks and costs to both the patient and the operator. By providing practitioners with 3D information on a device's position and orientation, a practitioner can more quickly and effectively perform an operation, thereby reducing some of these risks for both the patient and the practitioner.

In another example, 3D information (e.g., position information, orientation information) can be retrofitted to imaging devices that only provide 2D imaging data. For example, by using machine learning techniques to infer position and orientation information from 2D imaging data, imaging devices that are traditionally only capable of providing 2D imaging information can be augmented to provide 3D information without additional specialized hardware or components. This can enhance the operation of existing medical imaging devices at minimal expense.

The details of one or more embodiments are set forth in the accompanying drawings and the description below. Other features and advantages will be apparent from the description and drawings, and from the claims.

DESCRIPTION OF THE DRAWINGS

Like reference symbols in the various drawings indicate like elements

DETAILED DESCRIPTION

Figure 1:
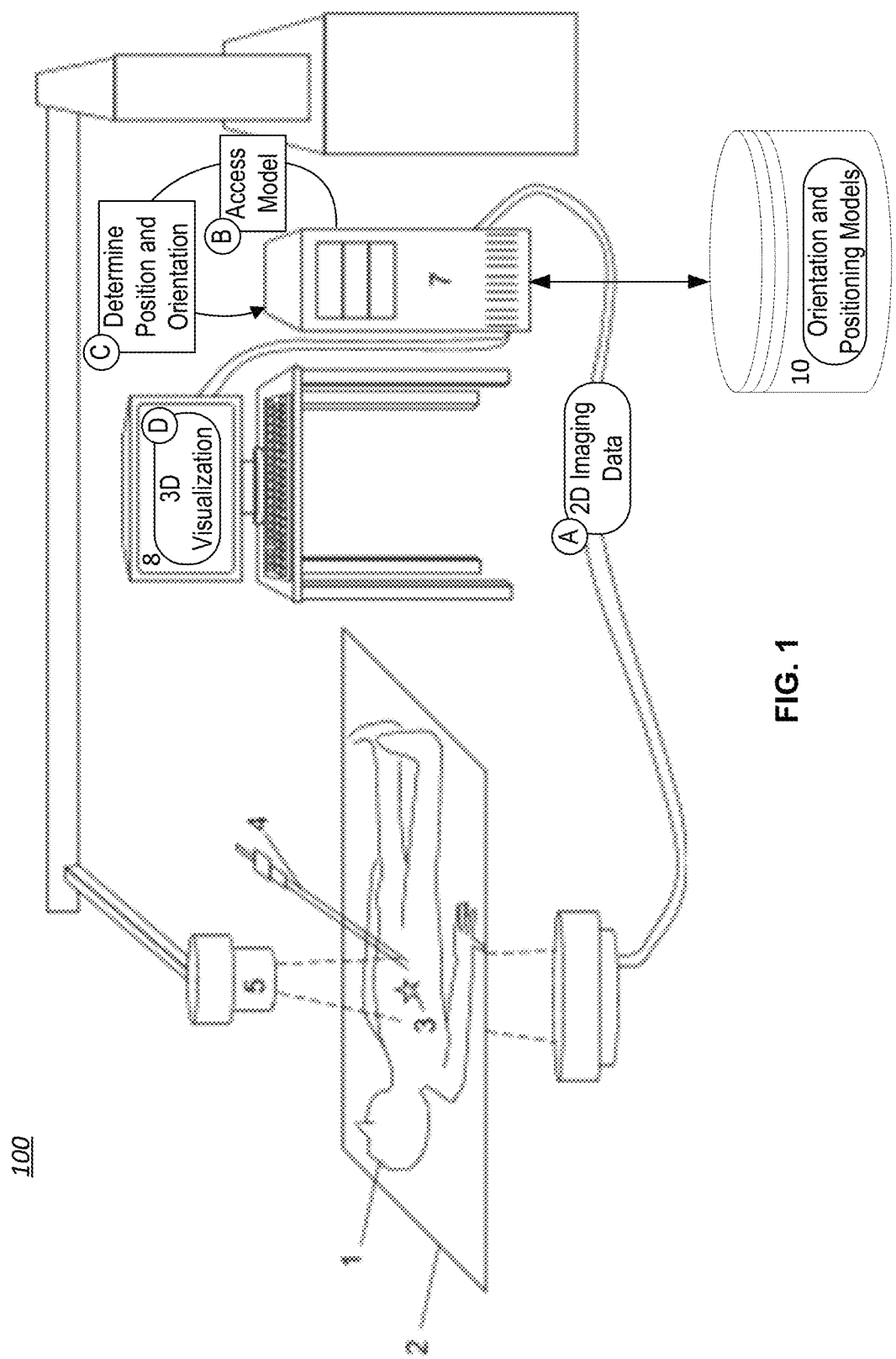
FIG. 1 is an example system for providing enhanced imaging of an example medical instrument.

In the following description of automatic invasive device orientation and position prediction technique embodiments, reference is made to the accompanying drawings, which form a part thereof, and show by way of illustration examples by which the automatic invasive device orientation and position prediction technique embodiments described herein may be practiced. It is to be understood that other embodiments may be utilized and structural changes may be made without departing from the scope of the claimed subject matter.

1.0 Automatic Invasive Device Orientation and Position Prediction

The following sections provide an introduction to the automatic invasive device orientation and position prediction technique embodiments described herein, as well as exemplary implementations of processes and an architecture for practicing these embodiments. Details of various embodiments and components are also provided.

As a preliminary matter, some of the figures that follow describe concepts in the context of one or more structural components, variously referred to as functionality, modules, features, elements, etc. The various components shown in the figures can be implemented in any manner. In one case, the illustrated separation of various components in the figures into distinct units may reflect the use of corresponding distinct components in an actual implementation. Alternatively, or in addition, any single component illustrated in the figures may be implemented by plural actual components. Alternatively, or in addition, the depiction of any two or more separate components in the figures may reflect different functions performed by a single actual component.

Other figures describe the concepts in flowchart form. In this form, certain operations are described as constituting distinct blocks performed in a certain order. Such implementations are illustrative and non-limiting. Certain blocks described herein can be grouped together and performed in a single operation, certain blocks can be broken apart into plural component blocks, and certain blocks can be performed in an order that differs from that which is illustrated herein (including a parallel manner of performing the blocks). The blocks shown in the flowcharts can be implemented in any manner.

1.1 Introduction

In general, automatic invasive device position and orientation prediction techniques described herein are capable of inferring a device's 3D orientation (roll, pitch, yaw) and 3D position (forward/back aka anterior/posterior, up/down aka cranial/caudal, left/right) from one or more 2D images of said devices. This can be accomplished, for example, via machine learning algorithms that learn, from 2D data, to correctly predict 3D information for a device, such as a device's position and orientation from a fixed or predefined origin and canonical orientation. Operation with machine learning algorithms can include, for example, (1) a training stage in which a machine learns to identify device positioning and orientation from annotated images of devices, and (2) an inference stage in which the now-trained machine infers a device's position and/or orientation from images that do not include the true position or orientation of the device (no annotations available). While the description below entails learning both a device's position and orientation, it applies equally well to learning to predict only a device's position or orientation as well.

Figure 5:
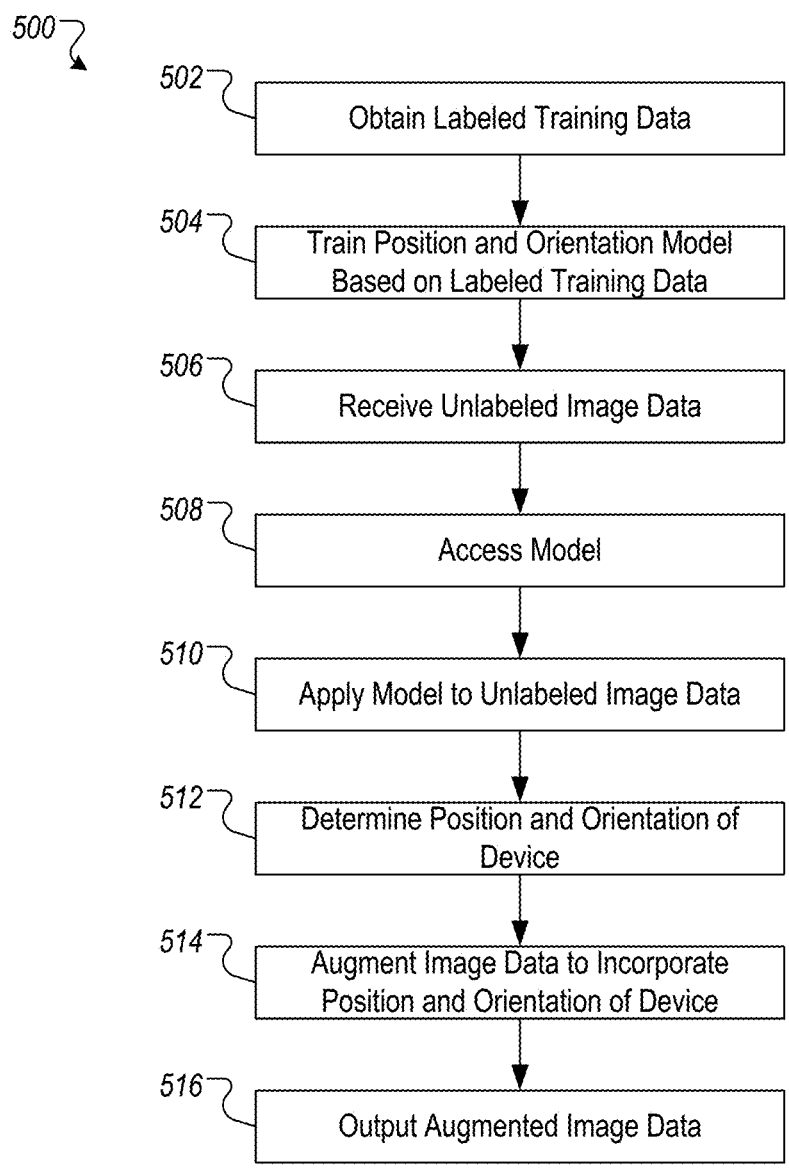
FIG. 5 is a flowchart of an example technique for performing automatic invasive device position and orientation predictions.

Automatic invasive device position and orientation prediction techniques are described below with regard to FIGS. 1 and 5. FIG. 1 is an example system 100 for providing enhanced imaging of an example medical instrument. FIG. 5 is a flowchart of an example technique 500 for performing automatic invasive device position and orientation predictions, for instance, using the example system 100 or other systems.

Referring to FIG. 1, the example system 100 can be trained to predict absolute or relative invasive object position and/or orientation. An example patient 1 is situated on an example operating table 2. An example invasive implement 3, such as filters, stents, drains, snares 4, and/or other devices are inserted into the patient 1. For instance, an IVC filter 3 and a snare 4 are depicted in FIG. 1. Other configuration and/or device/instrument/implement combinations are also possible. For example, system 100 can be used to determine the position and/or orientation of any surgical or invasive device(s).

An example imaging device 5 is positioned such that the invasive device(s) 3 can be imaged. For instance, the device 5 can be a fluoroscope that is used for imaging the device 3 and snare 4. The device 5 can be any imaging device, such as ultrasound, CT, MRI, and/or optical imaging device. The imaging device 5 sends and/or creates images (e.g., 2D imaging data) that are sent to a computer 7, as indicated by step A. For example, the imaging device 5 can transmit fluoroscopy data via a wired and/or wireless communications channel between the imaging device 5 and the computer 7. The computer 7 can be any of a variety of appropriate computing devices, such as a desktop computer, tablet computing device, embedded computing device, and/or mobile computing device that is capable of receiving the 2D imaging data as it is delivered from the imaging device 5. The computer 7 can access position and orientation models from a data repository 10 that are specific to the invasive devices 3, 4, and specific to the imaging device 5, as indicated by step B. Such models can have been trained by the computer 7 and/or other computer(s) prior to the imaging data being received, and can be continually updated/refined over time. The 2D imaging data can be applied to the model to determine position and orientation of the implement 3 and/or the device 4, as indicated by step C. The images can be annotated with position and/or orientation information to provide a 3D visualization of the implement 3 and/or the device 4 on a monitor 8 to an operator performing the operation, as indicated by step D.

For example, an operator can interact with the computer 7 to (a) initialize the tracking of the position and orientation of a single device 3 from its origin, or (b) initialize the tracking of the position and orientation between two devices 3, 4. Following initialization, as the imaging device 5 produces new images, the position and orientation requested by the operator are overlaid on top of the images produced and displayed on the monitor 8.

Figure 2:
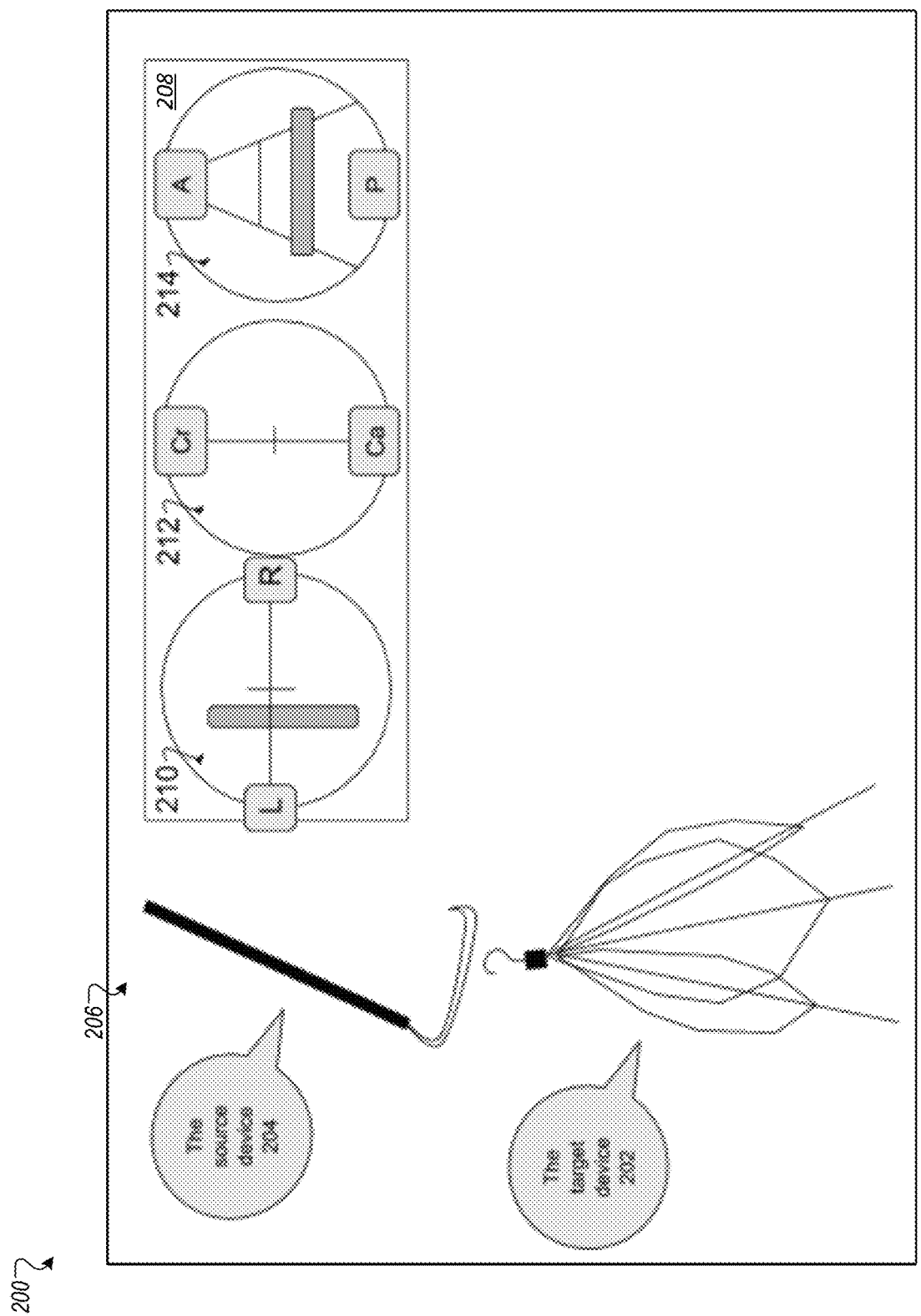
FIG. 2 depicts an illustration of the output of an imaging system (radiograph) overlaid with the output of the automatic orientation and translation prediction system.

FIG. 2 is a screenshot 200 of an example output of an imaging system (radiograph) overlaid with the output of an automatic orientation and translation prediction system, such as the system 100. For example, the screenshot 200 can be determined by the computer 7 and output on the monitor 8. In the depicted example, the screenshot 200 includes a target device 202 and a source device 204 that are identified in an example 2D image 206. A position and orientation model for the device used to produce the image 206 and for the target/source devices 202, 204, is retrieved and applied to the image 206 by the computer 7 to generate example orientation and position information 208. In the depicted example, the example information 208 includes visual guides to indicate 3D orientation and position of the devices 202, 204, such as visual left/right information 210, visual cranial/caudal information 212, and visual anterior/posterior information 214. Other visual 3D position information can additionally and/or alternatively be output as well, such as roll, pitch, and yaw information. Although the orientation and position information 208 is overlaid on the side of the 2D image 206 in this example, it can be incorporated and/or displayed with the image 206 in other ways, such as being used to generate real time 3D graphics depicting the devices 202, 204 within the patient's body.

1.2 Training

Given one or more images of an invasive device, where each image is annotated with the device's position and/or orientation, a machine learning algorithm can be trained to predict the position and orientation of the device that matches the annotation. For example, a supervised deep learning algorithm can be used to generate a model of the position and orientation of the device based on 2D images. Each image can be obtained from existing medical imaging techniques (e.g. x-rays, ultrasound, CT, MRI) and/or from computer generated imagery of such devices. In the former case, human annotators may provide per-image annotations of each device's position and orientation, whereas in the latter case, such annotations may be generated automatically (Section 1.2.1). In both cases, the labels do not annotate the pixels themselves, but rather exist as metadata to each image describing the relative positions and/or orientations of the devices in the image. Such annotations (e.g., labels) can be provided as inputs along with the images themselves to one or more machine learning algorithms that can use the inputs (e.g., images, annotations) to generate an imaging model that can be used to correctly predict 3D information for a device, such as a device's position and orientation from a fixed or predefined origin and canonical orientation.

For example, the example computer 7 can train one or more machine learning algorithms using annotated data (e.g., images, annotations) that is specific to the imaging device 5 and the invasive devices 3, 4. Sections 1.2.1-1.2.4 describe example techniques for obtaining annotated/labeled training data, as indicated by step 502 in FIG. 5. For example, images can be annotated with 3D orientation information (e.g., (roll, pitch, yaw) and position information (e.g., forward/back aka anterior/posterior, up/down aka cranial/caudal, left/right), which can be generated on real imaging data (e.g., images generated from a medical device being used on a patient) and/or from simulations (e.g., computer generated imagery to mimic real images). Real images can additionally and/or alternatively be annotated manually by qualified practitioners interpreting the images (see Sec. 1.2.3). Images generated from simulations can, by virtue of having been generated from a simulation, automatically provide orientation and/or position information for the images (see Sec. 1.2.2). In some implementations, invasive devices may already be equipped with components that provide some orientation and/or position information that could be incorporated into model training and for position/orientation determinations. For example, drains have included markers that help the operator know where side holes (where fluid enters the drain are) and the side holes are already present in a certain orientation on current devices. The position and orientation of such markers can be incorporated with and used as part of the techniques described in this document to determine device orientation and/or position on devices that are equipped to provide some orientation/position information, like the described drain in the preceding sentence.

1.2.1 Annotation of Images with Position and Orientation Information

To train a machine learning system to identify the position and orientation of one or more medical devices, a dataset can first be created that represents examples of said devices and their correct positions and orientations. Examples of such annotations include:

The position and orientation of a single device relative to a fixed origin. For example, in a sequence of images, the position and orientation of a device in any frame can be defined relative to the position and orientation of the device or fixed element in the first frame.

The position and orientation between two or more devices. For example, the distance (position) and relative orientations can be determined between an IVC filter and snare. An additional example relates to orientation of a guidewire with a previously placed stent.

1.2.2 Automatic Data Creation

To generate large amounts of labeled training data, computer generated imagery can be synthetically created to mimic real images. For example, CG modeling software can be utilized to create a 3D model of the invasive device and rendered using various photometric effects (blurring, synthetic occlusion) to mimic real medical images. This approach can enable the automatic creation of large numbers of images that are automatically labeled by the software that creates them. For example, a computer program can execute the rendering of a CG model of a single IVC filter at various positions and orientations. Because the computer program chooses (possibly randomly) the position and orientation at which to render the IVC filter, the position and orientation can therefore be automatically paired with the created image.

1.2.3 Manual Data Annotation

When manually creating a dataset of images, a medical practitioner or medical system can provide medical imagery with or without identifying marks or data. Such images can be labeled by one or more humans with the device's position and orientation.

1.2.4 Alteration of the Medical Device to Aid Inference

Figure 3:
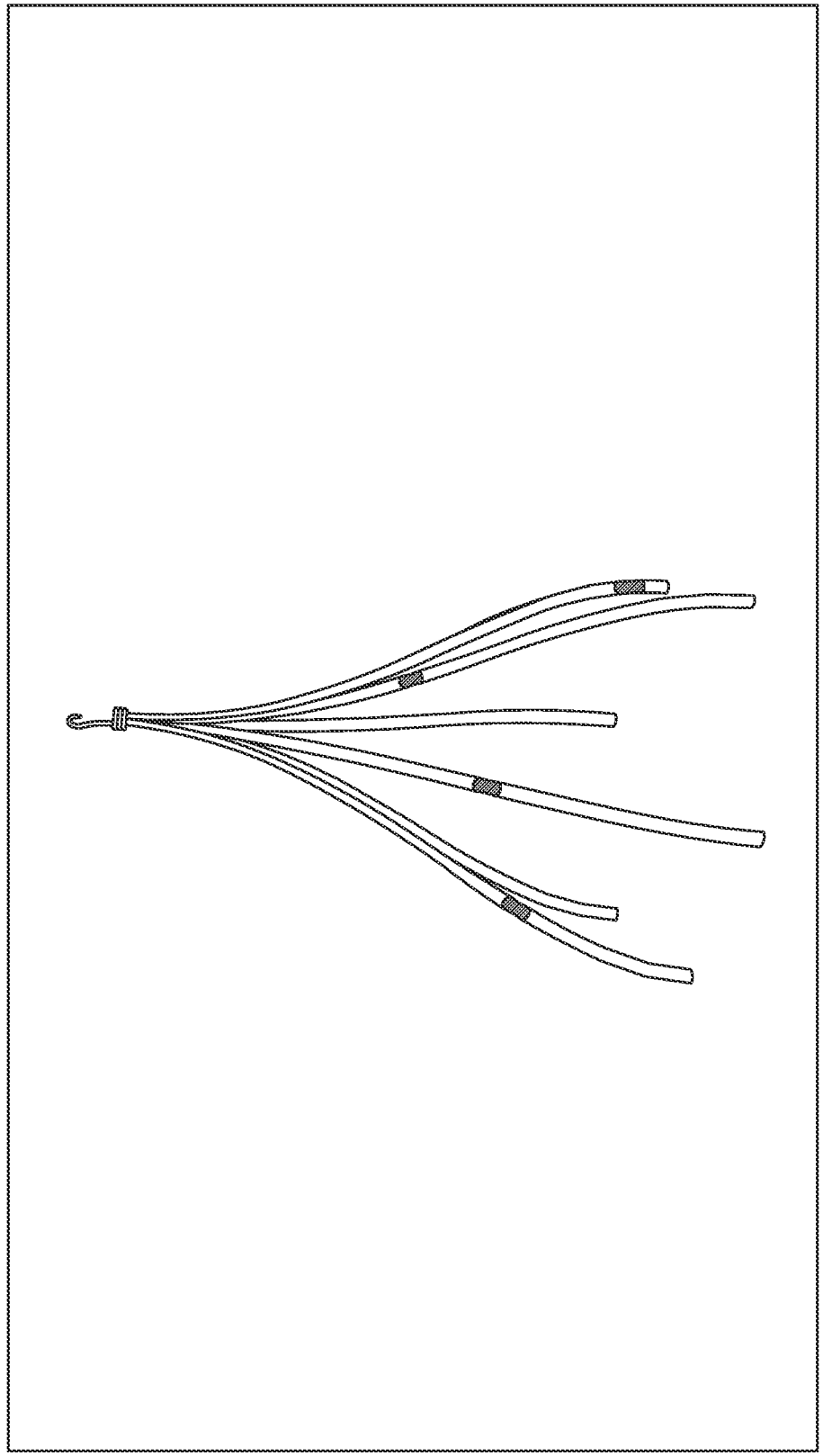
FIG. 3 depicts an IVC Filter with parts of the filter coated with alternative metals designed to absorb more or less of the emitted photons. This produces the effect of bands along the device of various grayscale intensities.
Figure 4:
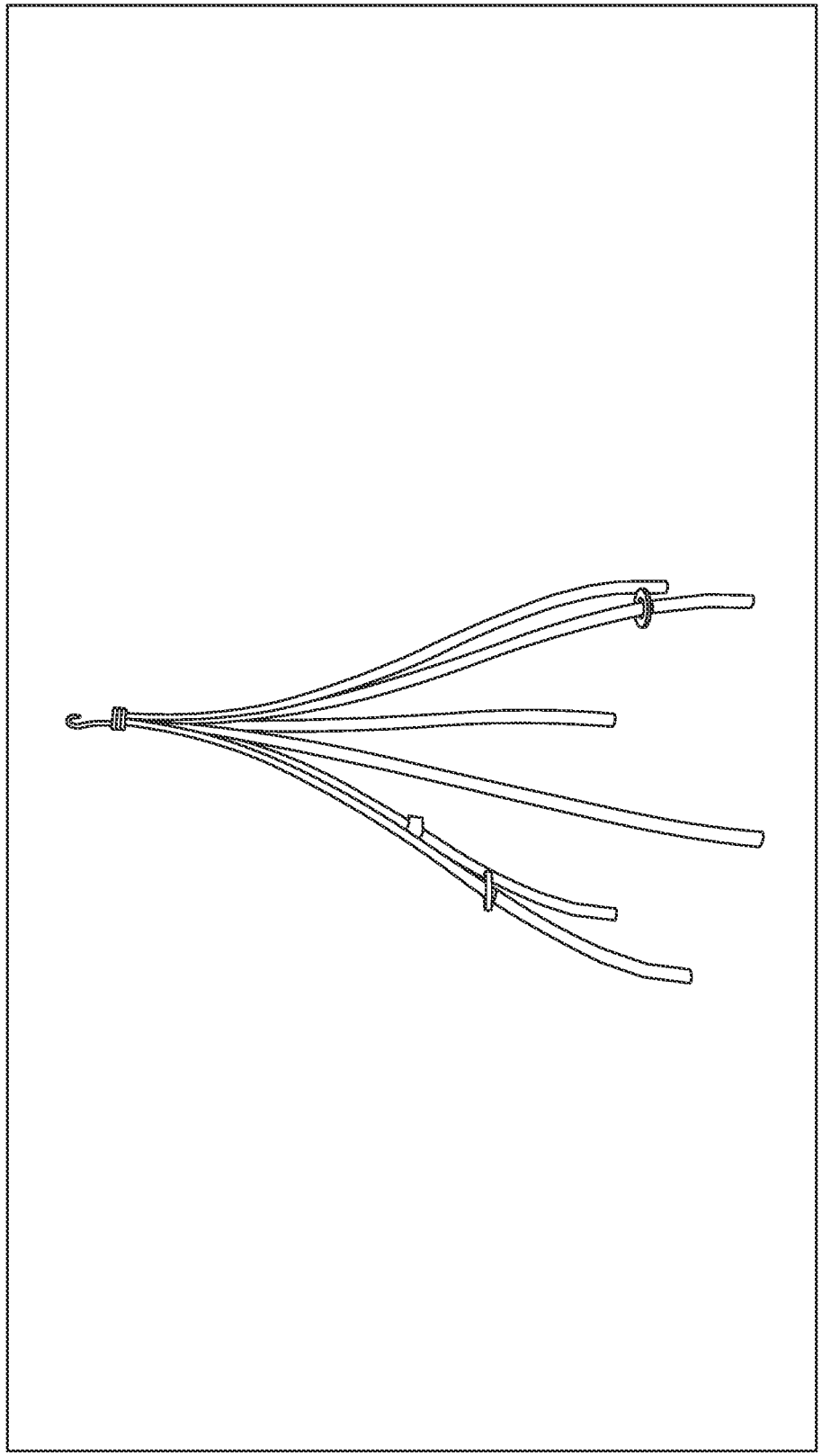
FIG. 4 depicts an altered IVC filter with additional metal protrusions which aid the ability to determine the orientation and position of the device.

In certain cases, the invasive devices themselves may be altered to ease the task of such automatic inference. For example, invasive medical devices can be altered by:

coating existing devices with radiation absorbing material, which can readily be detected and differentiated from other surfaces and/or objects that are not coated (FIG. 3), and designing devices with additional non-medical application other than aiding the ability to automatically orient and position the device (FIG. 4).

Additional, alternative, and/or other alterations of medical devices are also possible. Such medical device alterations can be used in combination with the machine learning described throughout this document to aid the machine in learning to predict device positions and orientations.

1.2.5 Example Machine Learning Model Architecture

Figure 6:
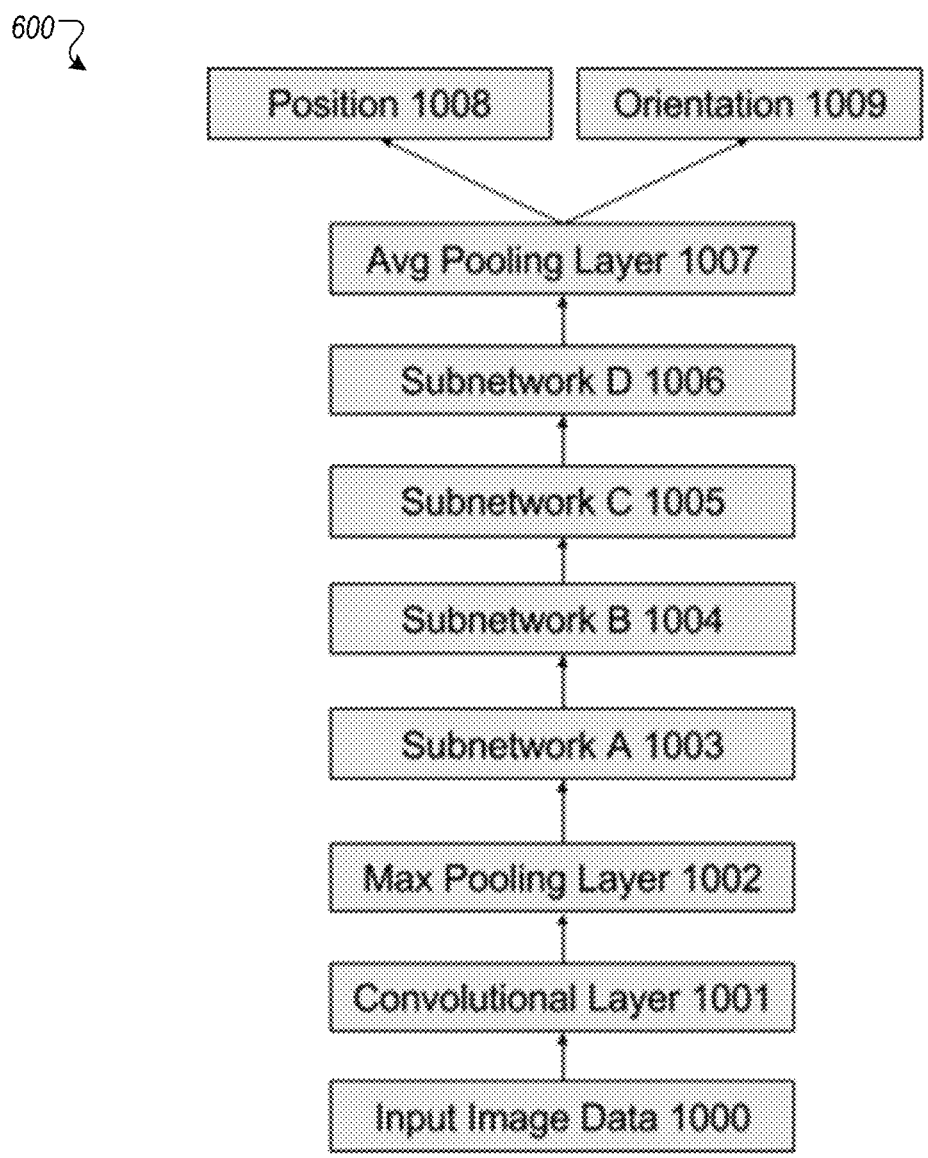
FIG. 6 is a block diagram of an example machine learning architecture.

Various machine learning architectures can be used and trained to predict relative position and orientations from imagery data, such as Deep Learning, Random Forests, AdaBoost and Support Vector Machines. FIG. 6 is a block diagram of an example machine learning architecture 600 that can be used and trained to predict relative position and orientations from imagery data. The example machine learning architecture 600 can be implemented on any of a variety of appropriate computing devices and systems, such as the computer 7 described above with regard to FIG. 1. The example architecture 600 can be used to perform one or more portions of the technique 500, such as training a model based on labeled training data (step 502) and/or applying a model to unlabeled image data (step 510) and determining the position and orientation of the device (step 512).

The example machine learning system 600 receives data characterizing an image input 1000, such as pixel data from an image of arbitrary size (e.g., 2D imaging data from the imaging device 5). The image is then fed through an example convolutional layer 1001, an example pooling layer 1002, an example set of residual layers 1003-1006, and another example pooling layer 1007 that can pool the resulting features into outputs, such as the position 1008 and orientation 1009 of a medical device (e.g., the device 4) captured in the imaging data. The machine learning system 600 can generate the position 1008 and orientation 1009 outputs so as to augment/enhance the imaging data, such as providing predictive position for the device along a third dimension (instead just two dimensions represented in the imaging data) and/or orientation of the device relative to one or more reference points, planes, or axes.

In instances where the architecture 600 is being trained to generate a predictive model, the position/orientation annotations for the input image data 1000 that are provided as training data are compared to the predictions for position 1008 and orientation 1009. The model's weights are then updated accordingly, using an optimization algorithm, such as Gradient Descent and/or the Adam Optimizer. When the architecture 600 has been trained and is being used with unannotated image data, the position 1008 and orientation 1009 that are output by the trained model provided by the architecture 600 can be used to supplement the image data in real time, for example, with on-screen annotations, overlaid graphics/annotations, and/or other graphical features.

Each of one or more convolutional layers 1001 can represent, for example, the convolution of a K×K set of N filters. These filters can be applied at each input location at a specified stride. For example, a stride of 1 indicates that each input is convolved with each K×K filter at that layer, whereas a stride of 2 indicates that every other input is convolved.

For example, the first convolutional Layer 1001 can include 64 7×7 filters and a stride of 2. The subsequent max pooling layer 1002 can use a 3×3 kernel of stride 2. The subsequent 4 residual layers (1003, 1004, 1005, 1006) can each use a subnetwork that takes the output from the previous stage as its input, performs a series of mathematical operations to that input, and produces a new transformed output. The output from the final subnetwork 1006 can be passed to an average pooling layer 1007 that produces a single vector of dimension 2048, for example. This vector is the model's transformed representation of the imaging data from which the position and orientation are predicted. The position 1008 and the orientation 1009 can be in any of a variety of formats. For example, the position (or offset) 1008 can be a vector of length 3 representing the distance between two objects in the input or the distance between one object and a fixed reference point. In another example, the orientation 1009 can be a vector of length 3 representing the roll, pitch and yaw between two devices or between the device and a fixed reference point. Other formats for the position 1008 and the orientation 1009 are also possible. The position 1008 and the orientation 1009 can be output in an interface presented in real time to a physician manipulating the device that is being imaged, like the example interface that is depicted in FIG. 2.

Figure 7:
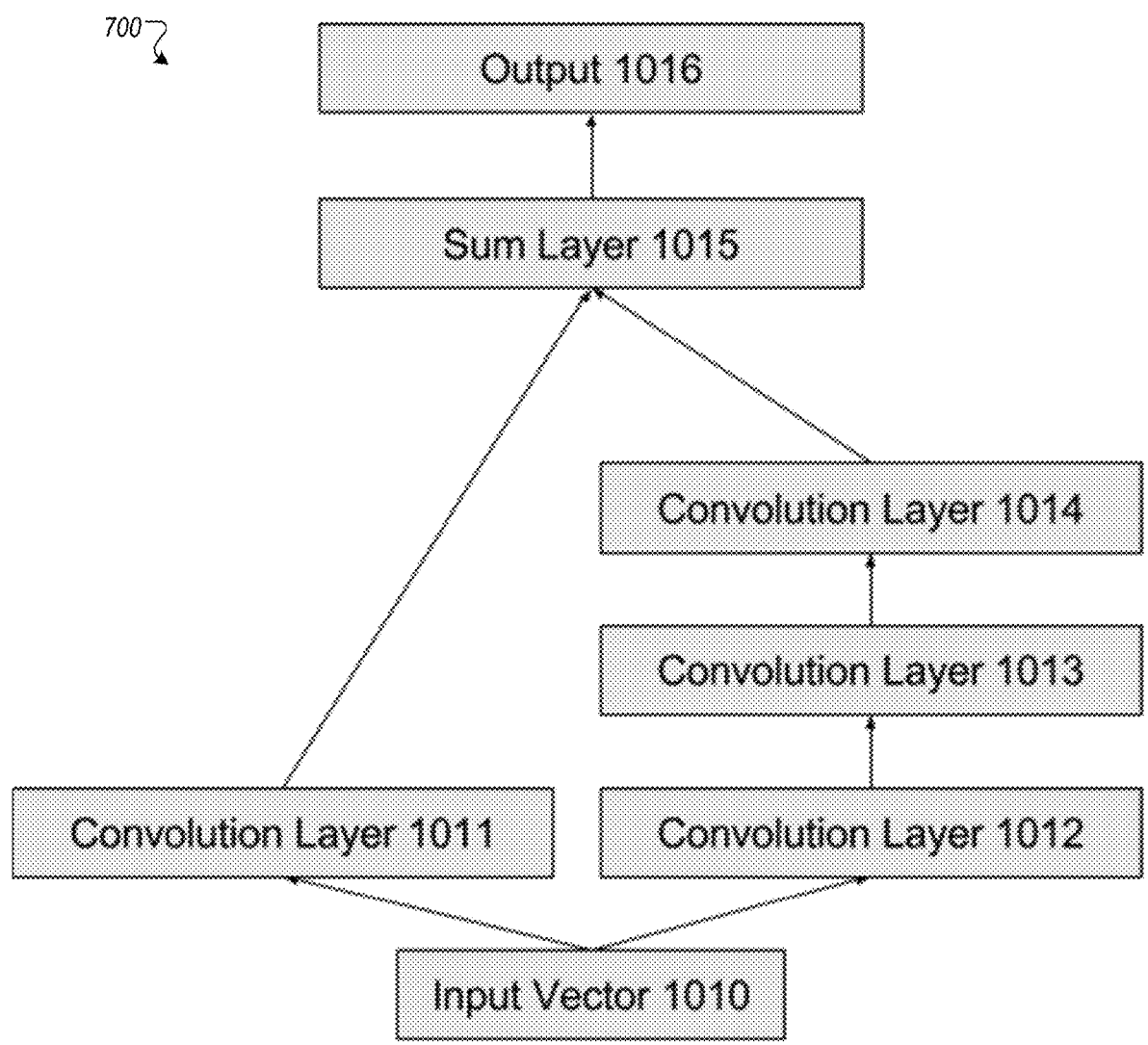
FIG. 7 is a block diagram of example subnetworks.

FIG. 7 is a block diagram of an example subnetwork 700, such as the subnetworks A, B, C and D (1003-1006) described above with regard to FIG. 6. For example, each of the subnetworks A-D (1003-1006) can be implemented using an architecture that is the same as or similar to the subnetwork 700. Some or all of the subnetworks A-D (1003-1006) can be implemented using other architectures.

The example subnetwork 700 can be defined using three parameters: the number of feature map outputs D, the number of feature maps in the bottleneck layers B, and the stride S used to compute the convolutions. The subnetwork 700 takes an input vector 1010, and performs a series of operations along multiple pathways. In a first example pathway (1011), a single 1×1 convolution 1011 with D filters is performed with stride S. In the second example pathway (1012-1014), a 1×1 convolution 1012 with B filters and stride 1 is performed, followed by a 3×3 convolution 1013 with D filters and stride S, followed by a 1×1 convolution 1014 with D filters and stride 1. The resulting vectors from each of the multiple pathways can be summed 1015 and passed through a nonlinear function, such as a rectified linear unit, to generate output 1016. The resulting output 1016 can be, for example, a vector of dimension D which represents the output of the subnetwork 700.

1.3 Inferring Position and Orientation Using a Trained Model

Inferring a device's position and orientation using a trained model (as described above) can be done in any of a variety of ways, such as through inferring the position and orientation of a device from a single image, inferring the position and orientation of a device from a single image given one or more reference images, and/or inferring the position and orientation of a device from a sequence of images. For example, a position and orientation model for the device can be trained on annotated/labeled data (e.g., single image, single image in light of reference images, sequence of images), as indicated by step 504 in FIG. 5 and described above. Such a model can then be used to infer position and orientation information from raw/unannotated image data. For example, image data (e.g., single image, single image and reference image, sequence of images) can be received (step 506), the trained model can be accessed (step 508), the model can be applied to the image data (step 510) to interpret the images and predict the position and orientation of an invasive device (step 512), and the predicted orientation and position information can be output (step 514). Examples of training a model to infer position and orientation information using different image data are described below in sections 1.3.1-1.3.3.

1.3.1. Inferring the Position and Orientation of a Device from a Single Image

To predict the position and orientation of a device from a single image, a dataset can be assembled containing a series of images, real or synthetic (CG), each of which can be annotated with the device's position and orientation. A machine learning algorithm, for example, a supervised deep learning algorithm, can then be trained to predict the position and orientation of the device in the image. The predicted orientation for roll, pitch and yaw can be in radian space, in which case a cosine distance loss function can be used. Alternatively, the roll, pitch and yaw may be discretized and a sigmoid-cross entropy can be used for training.

1.3.2 Inferring the Position and Orientation of a Device from a Single Image and a Reference Image To predict the position and orientation of a device from an image and a reference image, a dataset can be assembled containing pairs of images. Each pair can include a source image and a target image. The source image can be considered the reference image from which the position and orientation is measured. For example, the source image can be a device in a canonical or origin location/orientation. The target image can be of the same device, but translated and/or rotated. Each pair of images can be annotated with the translation and rotation of the device between the source and target images. A machine learning algorithm, for example, a supervised deep learning algorithm, can be trained to predict the position and orientation of the device in the image. The predicted orientation for roll, pitch and yaw can be in radian space, in which case a cosine distance loss function is used. Alternatively, the roll pitch and yaw can be discretized and a sigmoid-cross entropy used for training.

1.3.3 Inferring the Position and Orientation of a Device from a Sequence of Images To predict the position and orientation of a device from a sequence of images, a dataset can be assembled with image sequences. Each sequence (of one or more images) can be annotated with position and orientation labels. A machine learning algorithm, for example, a long short-term memory (LSTM) model, can be trained to predict the position and orientation of the device in the image. The predicted orientation for roll, pitch and yaw can be in radian space, in which case a cosine distance loss function is used. Alternatively, the roll pitch and yaw can be discretized and a sigmoid-cross entropy used for training.

1.4 Utilization of the Automatic Position and Orientation Prediction Between Multiple Devices An operator can use the aforementioned devices and prediction mechanism as follows. An invasive device(s) can be inserted into the patient and the imaging mechanism (e.g., x-ray, ultrasound, CT, MRI) is oriented towards the patient to produce initial imaging of the patient's internals and the invasive device. A computer can receive the output of the imaging mechanism (e.g., the raw 2D images themselves), as indicated by step 506. The computer can access a model trained on the imaging mechanism and the invasive device(s), as indicated by step 508. The model can be applied to the imaging data, as indicated by step 510, to interpret the images and predict the position and orientation of the invasive device(s) using the trained machine learning algorithm, as indicated by step 512. The predicted position and orientation can be used to augment the 2D imaging data (e.g., overlaid, provided adjacent to the 2D image), as indicated by step 514, and can be displayed to the practitioner, as indicated by step 516. For example, displaying this information can be done on a separate monitor or by overlaying the predictions on top of the raw images themselves.

Figure 9:
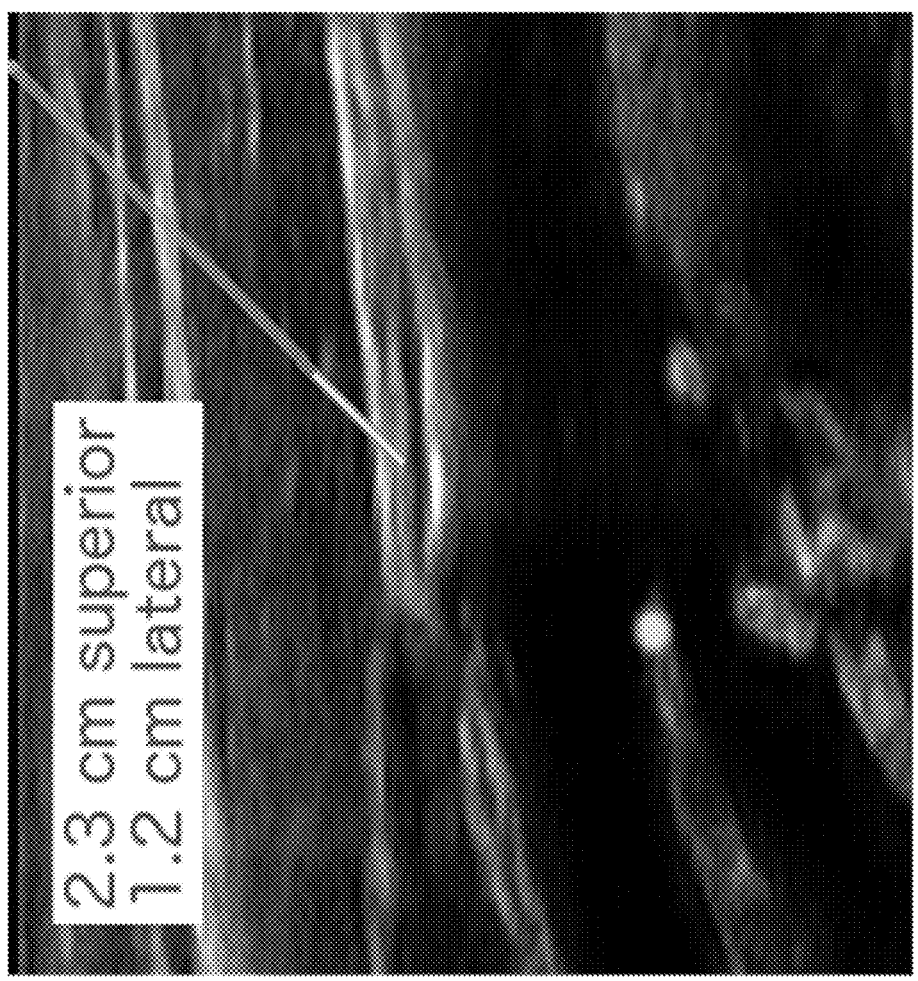
FIG. 9 is an example image of an invasive object being localized via imaging techniques.

FIG. 9 depicts example object inserted into the body such as a needle, wire, catheter, stent or probe, can be localized relative to a user-specified landmark (e.g. a lesion, specific part of a body, foreign body or second medical device (green dot) via any imaging modality such as fluoroscopy, ultrasound or MRI. Note that this does not require any specialized equipment nor materials used for the inserted objects and/or positioning of medically invasive devices, but instead provides additional information to assist in guiding the device through image analysis techniques described throughout this document.

Figure 8:
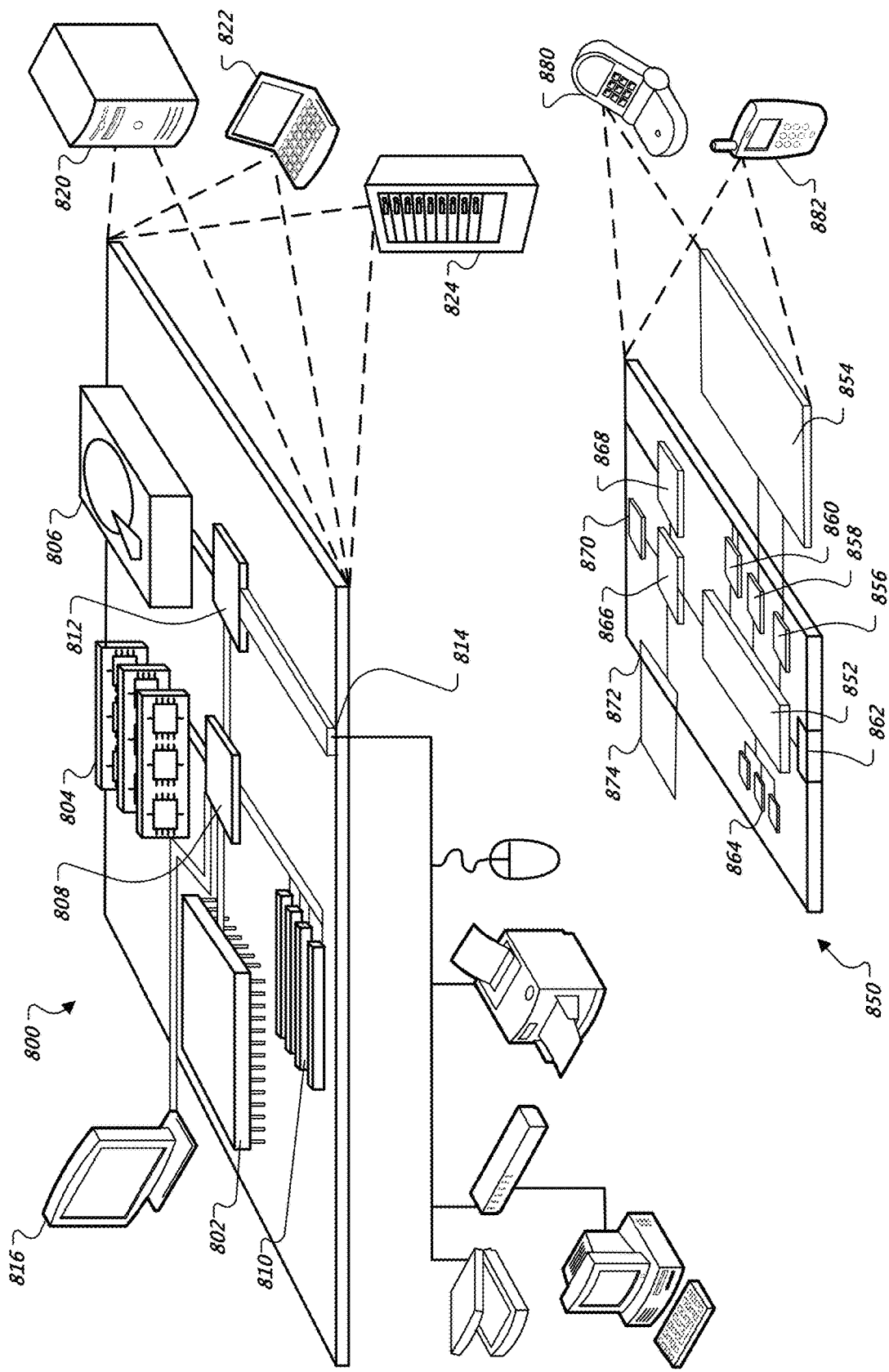
FIG. 8 is a block diagram of example computing devices.

FIG. 8 is a block diagram of computing devices 800, 850 that may be used to implement the systems and methods described in this document, as either a client or as a server or plurality of servers. Computing device 800 is intended to represent various forms of digital computers, such as laptops, desktops, workstations, personal digital assistants, servers, blade servers, mainframes, and other appropriate computers. Computing device 850 is intended to represent various forms of mobile devices, such as personal digital assistants, cellular telephones, smartphones, and other similar computing devices. Additionally computing device 800 or 850 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 800 includes a processor 802, memory 804, a storage device 806, a high-speed interface 808 connecting to memory 804 and high-speed expansion ports 810, and a low speed interface 812 connecting to low speed bus 814 and storage device 806. Each of the components 802, 804, 806, 808, 810, and 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as display 816 coupled to high speed interface 808, In other implementations, multiple processors and/or multiple buses may be used, as appropriate, along with multiple memories and types of memory. Also, multiple computing devices 800 may be connected, with each device providing portions of the necessary operations (e.g., as a server bank, a group of blade servers, or a multi-processor system).

The memory 804 stores information within the computing device 800. In one implementation, the memory 804 is a volatile memory unit or units. In another implementation, the memory 804 is a non-volatile memory unit or units. The memory 804 may also be another form of computer-readable medium, such as a magnetic or optical disk.

The storage device 806 is capable of providing mass storage for the computing device 800. In one implementation, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 804, the storage device 806, or memory on processor 802.

The high speed controller 808 manages bandwidth-intensive operations for the computing device 800, while the low speed controller 812 manages lower bandwidth-intensive operations. Such allocation of functions is exemplary only. In one implementation, the high-speed controller 808 is coupled to memory 804, display 816 (e.g., through a graphics processor or accelerator), and to high-speed expansion ports 810, which may accept various expansion cards (not shown). In the implementation, low-speed controller 812 is coupled to storage device 806 and low-speed expansion port 814. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. It may also be implemented as part of a rack server system 824. In addition, it may be implemented in a personal computer such as a laptop computer 822. Alternatively, components from computing device 800 may be combined with other components in a mobile device (not shown), such as device 850. Each of such devices may contain one or more of computing device 800, 850, and an entire system may be made up of multiple computing devices 800, 850 communicating with each other.

Computing device 850 includes a processor 852, memory 864, an input/output device such as a display 854, a communication interface 866, and a transceiver 868, among other components. The device 850 may also be provided with a storage device, such as a microdrive or other device, to provide additional storage. Each of the components 850, 852, 864, 854, 866, and 868, are interconnected using various buses, and several of the components may be mounted on a common motherboard or in other manners as appropriate.

The processor 852 can execute instructions within the computing device 850, including instructions stored in the memory 864. The processor may be implemented as a chipset of chips that include separate and multiple analog and digital processors. Additionally, the processor may be implemented using any of a number of architectures. For example, the processor 810 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 850, such as control of user interfaces, applications run by device 850, and wireless communication by device 850.

Processor 852 may communicate with a user through control interface 858 and display interface 856 coupled to a display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may be used to provide in communication with processor 852, so as to enable near area communication of device 850 with other devices. External interface 862 may provide, for example, for wired communication in some implementations, or for wireless communication in other implementations, and multiple interfaces may also be used.

The memory 864 stores information within the computing device 850. The memory 864 can be implemented as one or more of a computer-readable medium or media, a volatile memory unit or units, or a non-volatile memory unit or units. Expansion memory 874 may also be provided and connected to device 850 through expansion interface 872, which may include, for example, a SIMM (Single In Line Memory Module) card interface. Such expansion memory 874 may provide extra storage space for device 850, or may also store applications or other information for device 850. Specifically, expansion memory 874 may include instructions to carry out or supplement the processes described above, and may include secure information also. Thus, for example, expansion memory 874 may be used to provide as a security module for device 850, and may be programmed with instructions that permit secure use of device 850. In addition, secure applications may be provided via the SIMM cards, along with additional information, such as placing identifying information on the SIMM card in a non-packable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 864, expansion memory 874, or memory on processor 852 that may be received, for example, over transceiver 868 or external interface 862.

Device 850 may communicate wirelessly through communication interface 866, which may include digital signal processing circuitry where necessary. Communication interface 866 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 868. In addition, short-range communication may occur, such as using a Bluetooth, WiFi, or other such transceiver (not shown). In addition, GPS (Global Positioning System) receiver module 870 may provide additional navigation- and location-related wireless data to device 850, which may be used as appropriate by applications running on device 850.

Device 850 may also communicate audibly using audio codec 860, which may receive spoken information from a user and convert it to usable digital information. Audio codec 860 may likewise generate audible sound for a user, such as through a speaker, e.g., in a handset of device 850. Such sound may include sound from voice telephone calls, may include recorded sound (e.g., voice messages, music files, etc.) and may also include sound generated by applications operating on device 850.

The computing device 850 may be implemented in a number of different forms, as shown in the figure. For example, it may be implemented as a cellular telephone 880. It may also be implemented as part of a smartphone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. Moreover, other mechanisms for performing the systems and methods described in this document may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

The invention claimed is:

1. A system for augmenting imaging data depicting an invasive medical device, the system comprising:
   an invasive medical device configured to be inserted into a patient as part of a medical procedure;
   an optical imaging sensor configured to generate one or more images of the invasive medical device within the patient, wherein the optical imaging sensor is separate from the invasive medical device and is capable of being positioned at a vantage point relative to the patient from which the one or more images of the invasive medical device within the patient are captured;
   a database programmed to store a trained model for the invasive medical device, wherein the trained model was generated from one or more machine learning algorithms being trained on annotated images of the invasive medical device with orientation and distance information, wherein the trained model is programmed to be used to determine orientation and distance information from unannotated images of the invasive medical device;
   an imaging computer system that is programmed to:
      receive the one or more images of the invasive medical device from the optical imaging sensor,
      access the trained model for the invasive medical device from the database,
      determine a current orientation and a current distance of the invasive medical device within the patient by applying the trained model to the one or more images of the invasive medical device, and
      output the current orientation and the current distance of the invasive medical device; and
   a display to monitor the invasive medical device within the patient, the display being programmed to output (i) the one or more images of the invasive medical device as captured by the optical imaging sensor from the vantage point of the optical imaging sensor relative to the patient, and (ii) visual orientation information representing the current orientation of the invasive medical device within the patient and visual distance information representing the current distance of the invasive medical device within the patient, as determined from application of the trained model to the one or more images.

2. The system of claim 1, further comprising:
   a training computer system to generate the trained model for the invasive medical device, the training computer system being programmed to:
      obtain the annotated images of the invasive medical device with orientation and distance information, the annotated images depicting the invasive medical device within a patient, the orientation and distance information identifying orientations and distances of the invasive medical device in the annotated images,
      iteratively train a model for the invasive medical device by correlating each of the annotated images to corresponding orientation and distance information across one or more model layers using the one or more machine learning algorithms, wherein the iterative training generates the trained model for the invasive medical device, and
      store the trained model for use by the imaging computer system.

3. The system of claim 2, wherein at least a portion of the annotated images are actual images from use of the invasive medical device that have been manually annotated by a practitioner with distance and orientation information.

4. The system of claim 2, wherein at least a portion of the annotated images are computer generated images simulating use of the invasive medical device within patients as imaged by the optical imaging sensor.

5. The system of claim 2, wherein the one or more machine learning algorithms comprises a supervised deep learning algorithm.

6. The system of claim 2, wherein the trained model comprises a long short-term memory model.

7. The system of claim 1, wherein the optical imaging sensor is a LiDAR scanner.

8. The system of claim 1, wherein:
   the trained model is specific to the combination of the invasive medical device and the optical imaging sensor, and
   other trained models are used for other combinations of (i) the invasive medical device or other invasive medical devices and (ii) the optical imaging sensor or other imaging devices.

9. The system of claim 8, wherein the other imaging devices include an x-ray imaging device configured to generate one or more x-ray images.

10. The system of claim 8, wherein the other imaging devices include an ultrasound device configured to generate one or more ultrasound images.

11. The system of claim 8, wherein the other imaging devices include a computerized tomography ("CT") imaging device configured to generate one or more CT scans.

12. The system of claim 8, wherein the other imaging devices include a magnetic resonance imaging ("MRI") device configured to generate one or more MRI images.

13. The system of claim 1, wherein:
   the current orientation comprises a current roll, pitch, and yaw of the invasive medical device, and
   the visual orientation information includes visual roll information, visual pitch information, and visual yaw information that is presented in the display with the one or more images and the visual distance information.

14. The system of claim 13, wherein the current roll, pitch, and yaw is in radian space, and the trained model is determined using a cosine distance loss function.

15. The system of claim 13, wherein the current roll, pitch, and yaw is discretized and the trained model is determined using a sigmoid-cross entropy.

16. The system of claim 1, wherein:
   the current distance comprises (i) anterior and posterior distance information, (ii) cranial and caudal distance information, and (iii) left and right distance information, and the visual distance information includes visual anterior and posterior distance information, visual cranial and caudal distance information, and visual left and right distance information that is presented in the display with the one or more images and the visual orientation information.

17. The system of claim 1, wherein the current orientation and distance of the invasive medical device is determined from a single image from the one or more images.

18. The system of claim 1, wherein the current orientation and distance of the invasive medical device is determined from a single image from the one or more images and a reference image for the invasive medical device, wherein the reference image is generated by a second imaging device.

19. The system of claim 18, wherein the second imaging device is at least one of an ultrasound imaging device, a CT imaging device, an MRI imaging device, an x-ray imaging device, or a nuclear imaging device.

20. The system of claim 1, wherein the distance information is a position of the invasive medical device within the patient.

\* \* \* \* \*